United States Patent [19]

Mercer et al.

[11] Patent Number: 4,460,338
[45] Date of Patent: Jul. 17, 1984

[54] PLASTERLESS DENTAL ARTICULATOR AND METHOD FOR MOUNTING CASTS

[76] Inventors: Roger W. Mercer, 1340 Arlington Dr., Fairborn, Ohio 45324; Louis E. Hay, 847 Woodhill Rd., Dayton, Ohio 45431

[21] Appl. No.: 400,975

[22] Filed: Jul. 22, 1982

[51] Int. Cl.³ .................................................. A61C 11/00
[52] U.S. Cl. .............................................. 433/60; 433/75
[58] Field of Search ............... 433/57, 58, 60, 61, 433/62, 63, 64, 65, 66, 67, 75, 76

[56] References Cited

U.S. PATENT DOCUMENTS

| | | | |
|---|---|---|---|
| 1,668,845 | 5/1928 | Hanau | 433/59 X |
| 2,365,475 | 12/1944 | Klein | 433/60 |
| 2,765,533 | 10/1956 | McMorris | 433/60 |
| 4,128,942 | 12/1978 | Schleich | 433/65 X |
| 4,358,269 | 11/1982 | Hay et al. | 433/60 |
| 4,371,338 | 2/1983 | Mercer et al. | 433/60 |

Primary Examiner—Robert P. Swiatek
Attorney, Agent, or Firm—Louis E. Hay

[57] ABSTRACT

A mechanically adjustable articulator for mounting poured dental casts used in the fabrication of dentures without the use of mounting plaster, the articulator having central locating pins for entering drilled apertures in the base of the casts, and further having adjustable retaining screws which enter drilled apertures in the perimeter of the casts to retain the casts in fixed position after which the casts may be adjusted to any desired relationship with each other; and a method for drilling and mounting the casts, including a drill jig useful for such purpose.

23 Claims, 11 Drawing Figures

PLASTERLESS DENTAL ARTICULATOR AND METHOD FOR MOUNTING CASTS

REFERENCE TO RELATED U.S. PATENT APPLICATIONS

Ser. No. 056,536 Dental Articulator Having Simplified Means For Mounting Dental Casts—Mercer et al, filed July 11, 1979 and now U.S. Pat. No. 4,371,338.

Ser. No. 241,580 Plasterless Mounting Dental Articulator—Hay et al, filed Mar. 9, 1981 and now U.S. Pat. No. 4,358,269.

BACKGROUND OF THE INVENTION

Dental articulators are a common and necessary apparatus in the fabrication of a dental prosthesis. Stripped to its bare essentials, the process of fabricating a prosthesis commences when the dentist takes impressions of the patient's maxillary and mandibular arches which may or may not include natural teeth. These impressions are negative imprints of the arches and become the molds into which the raw material for forming positive dental casts is poured. These positive casts are replicas of the patient's arches (with or without teeth) and become the primary form on which the prosthesis is to be constructed.

In order to construct an acceptable prosthesis, these dental casts are normally mounted in an articulator in order that the maxillary and mandibular casts are maintained in the same anatomical relationship as in the mouth of the patient. This is true in all cases, even those where only one prosthesis, as for example, the maxillary arch is to be constructed; since the prosthesis must also conform with the relating surfaces on the mandibular arch in the patient's mouth.

Another reason why the dental casts are mounted in the articulator is to permit arrangement of the denture (false) teeth in their proper position for occlusion. On partial dentures, the occlusion of the denture teeth must be with natural teeth. On full dentures greater liberty is often taken to improve function and asthetics. The desired occlusion not only includes the vertical bite, but also a degree of lateral movement as well as posterior and anterior movement of the lower jaw. These various movements are produced by the temporomandibular joint which is the joint formed by the condyle of the mandible and the temporal bone. Many dental articulators are built to simulate these movements to a high degree.

Past practice for countless years has been to mount the dental casts in the articulator by means of plaster which is usually a gypsum material. This locates the dental casts in a fixed position. Mounting the dental casts by means of plaster is relatively expensive, is dusty and time consuming because the powdered raw material must be thoroughly mixed with a liquid and the plaster must be allowed to set, the process is subject to error which cannot be compensated, and all utensiles must be thoroughly cleaned after each use. Even in cases where the dental casts have been provided with grooves to facilitate removal and remounting which is usually a requirement in the fabricating process, it is questionable, at best, whether or not the casts are remounted to their precise originally mounted positions.

On the order of 95% of all dental articulators built to date have been built to use with the plaster mounting techniques. A few have been built which are mechanical mounting devices such as claws or other clamping devices in an attempt to find a better mounting technique than by the use of plaster. These alternate mounting techniques have been far less satisfactory than plaster, especially in those situations where the dental casts are to be removed and remounted to their original positions.

The principal cause for the difficulty was that the casts were retained in a manner which did not have firmly established locating positions; therefore, the casts could not be remounted to their precise original positions in the articulator. The first known articulator in which the casts could be remounted to their precise original position by means other than the plaster mounting articulators is the articulator taught in applicants' U.S. Pat. No. 4,315,740 Apparatus For Mounting Dental Casts in which this was accomplished by means of threaded apertures in the base of the casts; one method for forming the threaded apertures being taught in U.S. Pat. No. 3,975,489 Mercer. Applicants' U.S. Pat. No. 4,242,292 teaches another method for forming a threaded aperture in the base of a dental cast.

Applicants' referenced patent applications teach other methods of mounting dental casts without the use of mounting plaster. This is accomplished by using protruding pins in the articulators which slip-fit into apertures in the base of the casts to prevent any horizontal movement of the casts on their mounting plates. Vertical and rotational movement on the mounting plates is prevented by clamping or holding means acting on the perimeter of the casts. In some designs, the holding means include cutters which form detents in the perimeter of the casts.

As will be shown, the articulator constituting the present invention has certain mechanical changes in the construction details and the manner in which the articulator is adjusted; in a drill jig for forming the apertures in the dental casts to be mounted; and, in the technique for drilling the apertures and mounting the casts.

SUMMARY OF THE INVENTION

The preferred embodiment of the present invention mounts poured dental casts, used in the fabrication of dentures, by means of central locating pins which protrude from the cast mounting plates and slip-fit into an aperture in the base of each cast. Each cast is held in fixed position on the mounting plate by means of an adjustable mounting screw which has a spherical end for engaging a spherical cavity or detent cut into the perimeter of each cast. The combination of a locating pin and a mounting screw holds each cast in fixed position on its mounting plate.

The cavity in the perimeter of the cast is cut to be in radial alignment with the axis of the locating pin on which the cast is positioned, and the longitudinal axis of the mounting screw is in like alignment. This radial alignment permits the cast to be removed from the articulator and remounted to its precise original position, regardless of the number of times the cycle is repeated.

It has been found that, if the mounting screw is inclined at about 10 degrees from the horizontal so as to apply a vertical thrust component in the direction which will bias the cast toward the mounting face on the mounting plate, there is no possibility for the cast not to make firm seating contact on the mounting plate. Proper positioning of the cavity in the perimeter of the cast in relationship with the cavity in the base is assured by using the drill jig which will be described below.

The articulator is fully adjustable for the five movements required for positioning matched upper and lower dental casts in their centric occlusal position which is the position at which the dentures are to be fabricated. As viewed from the front of the articulator, the five mechanical movements are: (1) longitudinal movement; (2) lateral movement; (3) vertical movement; (4) rotary movement; and, (5) canting movement to any compound angle, preferably to about 30 degrees in order to meet severe conditions.

DESCRIPTION OF THE PREFERRED EMBODIMENT

Figure 1:
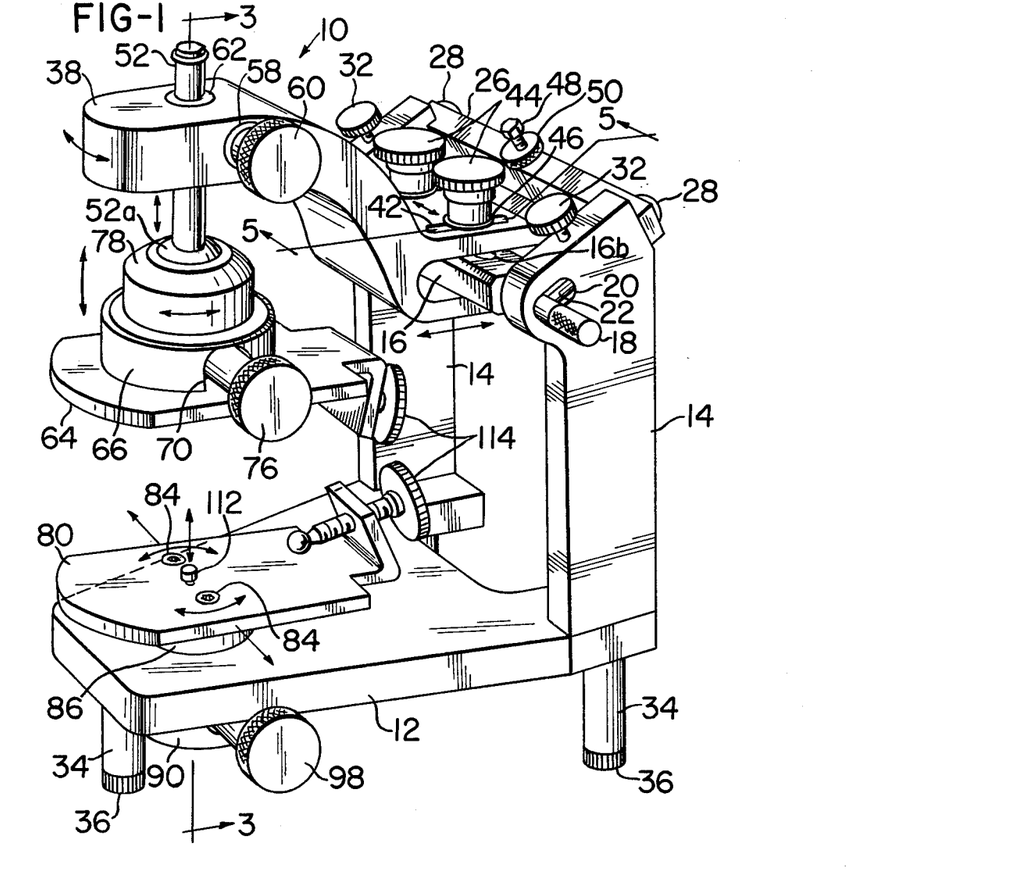
FIG. 1 is a vertical perspective of the articulator having a lower mounting jig which is laterally, vertically and rotationally adjustable.
Figure 2:
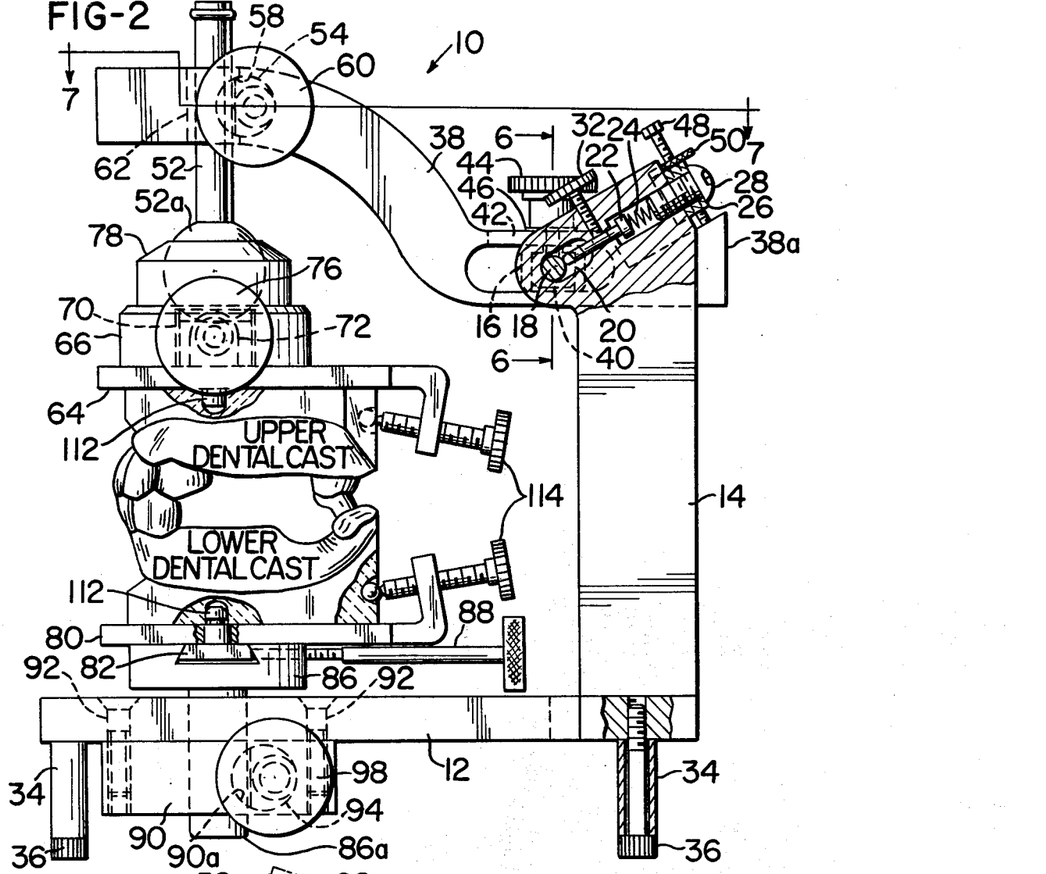
FIG. 2 is a side elevation of the articulator depicted in FIG. 1.
Figure 3:
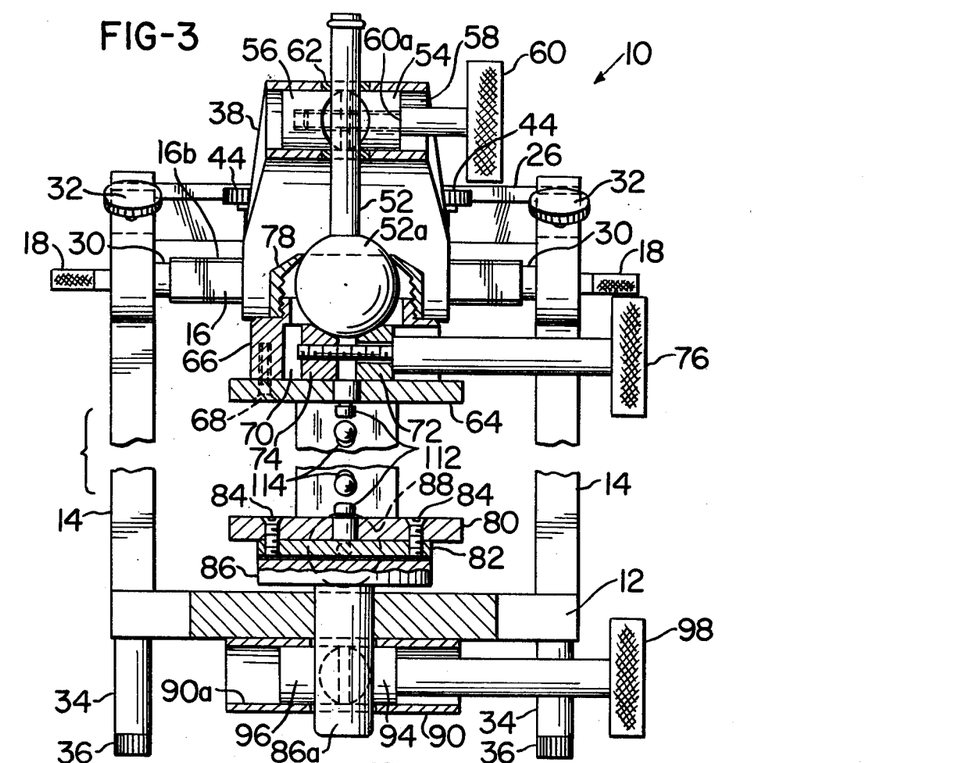
FIG. 3 is a vertical cross-section taken on line 3—3 of FIG. 1.
Figure 4:
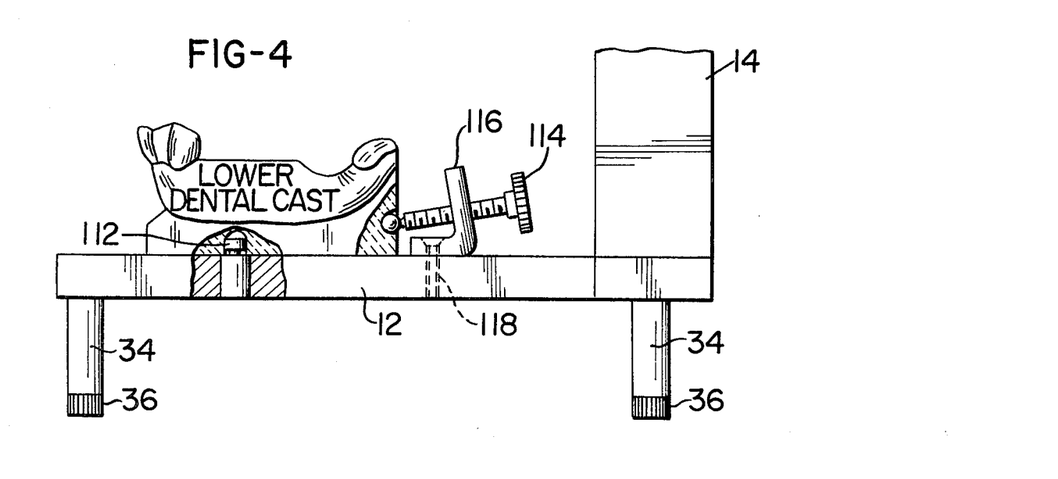
FIG. 4 is a partial side elevation of the lower portion of the articulator having a lower mounting jig which is non-adjustable.

At the onset it should be noted that there are several species of the articulator depicted in the drawings. The principal variations are in the lower cast mounting jigs. FIG. 4 depicts the most simple species in which the lower dental cast is mounted onto the base element of the articulator and is non-adjustable. The most complex species is depicted in FIGS. 1-3 and may be made to be laterally, vertically and rotatably adjustable. The dove tail slide 82 and the screw 88 which are shown in FIG. 2 are hidden by the mounting plate 80 in FIG. 1. The intermediate species of lower mounting jig omits the dove tail slide 82 and is vertically and rotatably adjustable. The upper dental cast mounting jig may be the same for all species of the articulator which have been depicted.

Specific reference is made to FIGS. 1-2 which depict complete articulators. FIG. 2 depicts upper and lower dental casts mounted in the articulator. The dental casts have been omitted in FIG. 1 to better depict construction details, and to more easily indicate the various movements of the upper and lower mounting jigs.

It is noted in FIG. 2 that the dental casts are adjusted to their centric occlusion position in which the few remaining natural teeth shown are in their normal bit position. The dentures to be fabricated are upper and lower partials fitting in the portions of the dental arches which no longer have any natural teeth.

The articulator 10 has a frame comprising a base element 12, vertical elements 14 and a normally horizontal leaf element 16 which is pivotally supported at the upper end of the vertical elements by means of actuating pins 18 which are pressed or screwed into the ends of leaf element 16. As best seen in FIG. 1, the actuating pins 18 are movable in condyle slots 20, the purpose of which is well known to the art and have no novelty per se.

The leaf element 16 is biased to the forward position depicted by means of a plunger pin 22 acted upon by a biasing compression spring 24. The head of the plunger pin 22 and compression spring 24 are retained within a counterbore in the vertical element 14 by means of a cross-bar 26, which is most easily seen in FIGS. 1, 3, 5 and 6. The cross-bar 26 is held in position by screws 28 which attach the cross-bar at the upper ends of the vertical elements 14.

There is a plunger pin 22 and compression spring 24 acting on each of the actuating pins 18. The cross-bar 26 spans the space between the two vertical elements 14 and holds the vertical elements in rigid alignment.

Figures 6, 7:
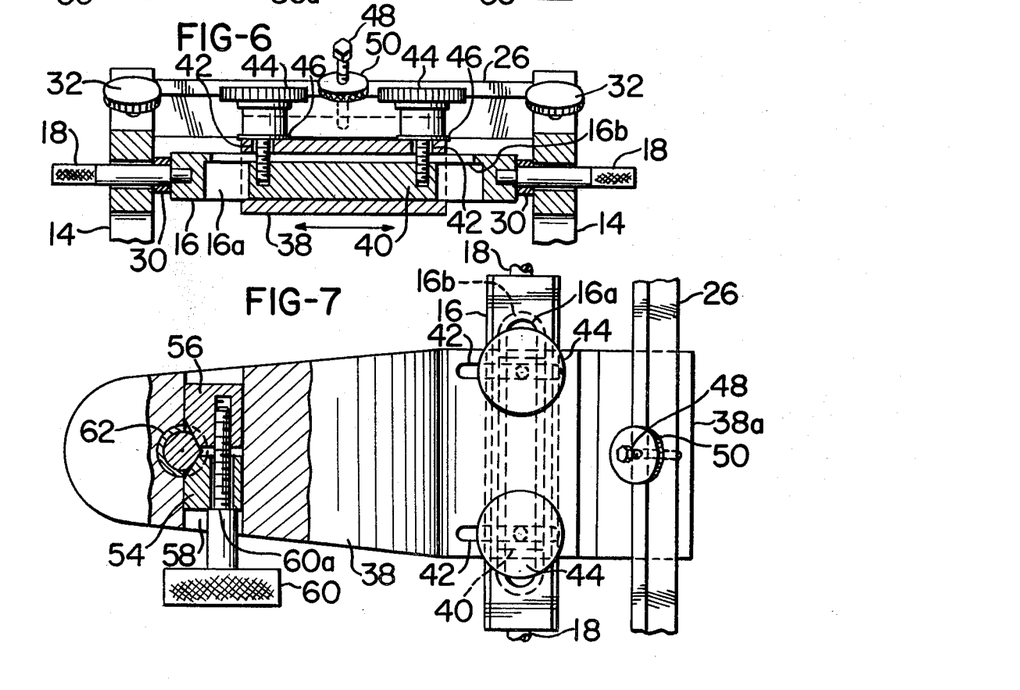
FIG. 6 is a vertical cross-section taken on line 6—6 of FIG. 2 and showing construction details.
FIG. 7 is a plan view, partially in cross-section, taken on line 7—7 of FIG. 2.

As best seen in FIGS. 3 and 6, washers 30 of varying thickness are used in adjusting out any end play of the leaf element 16 in relationship with the vertical elements 14. Ideally, there should be no end play, and nylon washers have been found to be excellent for the purpose of adjusting out any end play.

Within the limits of the movement permitted by the length of the condyle slots 20 as depicted in FIG. 1, the leaf 16 may be releasably held in any desired position by means of screws 32 which act against plunger pins 22 as most clearly seen in FIG. 2. The function of the condyle movement is well known in the art, for which reason it requires no further discussion. Within the scope of the invention, the condyle movement may be omitted, as is often done on more simple articulators.

The articulators are provided with suitable feet. The feet may be made integral with the base element 12; or, they may be made of sleeves 34 which are held in position by means of socket head screws 36 as shown. The principal purpose of the feet is to raise the work area of the articulator a greater distance above the work bench on which the articulator is used. It is easier for technicians to work when the work area of the articulator is not too close to the top of the work bench.

The upper cast mounting jig comprises the principal elements depicted at the upper portion of the articulator which are not directly related to the frame elements, and to the leaf which is normally associated with the frame elements.

The upper cast mounting jig has a body element 38 which, as depicted in FIGS. 1 and 2, is of general bowed shape with the front portion thereof substantially parallel with, but at a higher elevation than the rear portion of the body element. There is a technical reason for this construction associated with the movement of engaging and disengaging teeth when the jaw commences to open. This movement is well known to the art, for which reason it requires no further discussion.

Figure 5:
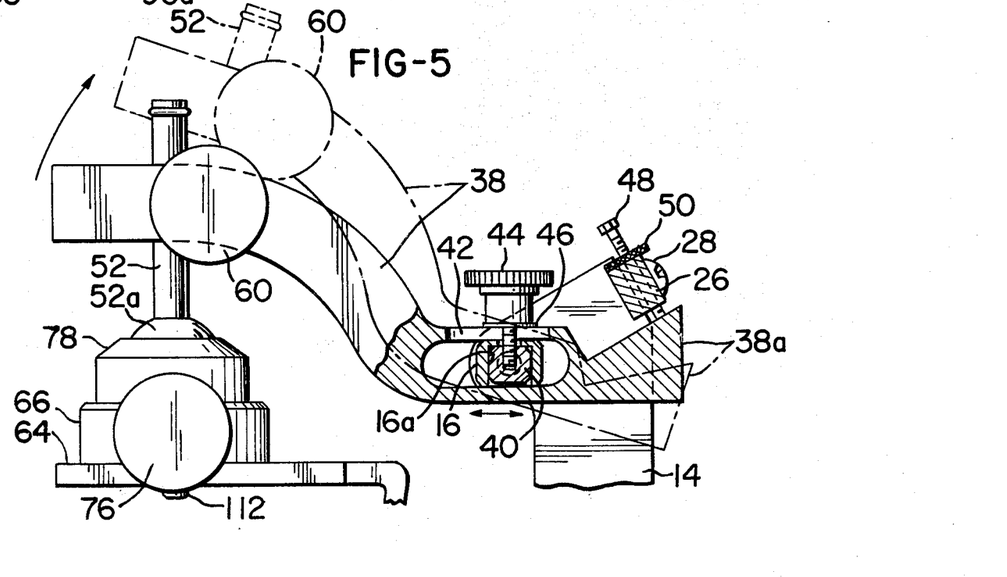
FIG. 5 is a partial elevation of the upper portion of the articulator, partially in section, which is typical of all species of the articulator.

The rear parallel portion of the body element 38 is machined to have a transverse longitudinally elongated slot therethrough as best seen in FIG. 5. On assembly, the leaf element 16 passes through the elongated slot, after which the actuating pins 18 are installed. The leaf element 16 and the body element 38 are now movably retained by the vertical elements 14.

The body element 38 is longitudinally and laterally adjustable on the leaf element 16 as depicted in FIGS. 5–7, and also has limited angular movement therewith. The bottom side of the leaf element is machined to contain an elongated slot 16a for receiving an elongated sliding block 40. As best seen in FIGS. 1, 5 and 7, the body element 38 contains two longitudinal slots 42 extending into the large transverse slot in the body element 38. A headed screw 44 passes through each of the longitudinal slots 42 and engages threaded apertures in the sliding block 40 as best seen in FIG. 6. Washers 46 should be used to prevent creep when the screws 44 are tightened. Tightening screws 44 pinches the sliding block 40 against the shoulder 16b in the leaf element 16 as depicted in FIG. 6.

When the screws 44 are loosened, the body element 38 may be positioned both laterally and longitudinally on the leaf element 16, which position is releasably retained when the screws 44 are tightened. When the screws 44 are loose, the body element 38 may also be adjusted angularly in relationship with the leaf element.

Specific reference is made to FIG. 5 in which the body element 38 is shown with an angular portion 38a extending rearward from the large transverse slot. An adjusting screw 48 extending through cross-bar 26 engages the top face of the angular portion 38a and thereby limits the amount of angular downward travel of the front portion of body element 38. The adjustment may be retained by means of a lock nut 50. After the dental casts are mounted in the articulator as depicted in FIG. 2, the adjustment is made to prevent excessive pressure on the casts. The angle of the top face of the angular portion 38a should be the same as the angle of the condyle slots 20.

Within the scope of the instant invention, the adjusting arrangement depicted at the rear of the articulator may be replaced by an incisal guidance pin extending downward from the front of the body element 38. There is no novelty per se in the adjusting arrangement depicted, or in incisal guidance pins on dental articulators.

The forward portion of the body element 38 has a vertical adjustment rod 52 having a ball 52a at the lower end thereof, the purpose of which will be explained below. The precise vertical position of rod 52 is releasably retained by a wedge clamping arrangement as best seen in cross-section in FIG. 7.

The clamping arrangement has two wedge blocks 54 and 56, both of which are externally circular for slip-fitting into a circular aperture 58 which is horizontally perpendicular to the vertical adjustment rod 52. Each of the two wedge blocks is machines to have a 45 degree face which engage 45 degree flats along the length of the vertical adjustment rod as depicted in FIG. 7. A shouldered adjusting screw 60 actuates the wedge blocks. The adjusting screw 60 has a threaded end which engages a threaded aperture in wedge block 56 after passing through a slightly larger aperture in wedge block 54. A shoulder 60a abuts against the adjacent face on wedge block 54, and as the screw 60 is tightened, the two wedge blocks are drawn together, which draws the 45 degree flats on the wedge blocks against the flats on the vertical rod 52. Since the wedge blocks are circular on the outside and are free to move longitudinally in the circular aperture 58, the wedge blocks are self-centering on the vertical rod. It is noted that the longitudinal axis of the adjusting screw is not on the longitudinal axis of the wedge blocks. This prevents any tendency of the wedge blocks from trying to rotate when the screw 60 is being actuated.

The body elements 38 have been built of aluminum and the vertical adjustment rod built of steel. Because of the large pressure applied by the wedge blocks 54 and 56 in forcing the vertical rod against the side of the aperture in the body element, it was found desirable to use a stainless steel bushing 62 as a means for preventing excessive clearance-producing wear. The bushing must have a transverse clearance slot cut in the wall which is adjacent to the wedge blocks which are also made of steel.

The remaining elements of the upper cast mounting jig are all movable on the ball 52a which is at the lower end of the vertical adjusting rod 52. A cast mounting plate 64 is attached to a sleeve 66 by means of a plurality of screws 68 as shown in FIG. 3. The sleeve 66 has a circular aperture 70 which is comparable to the previously described circular aperture 58 and contains wedge blocks 72 and 74 which are comparable to previously described wedge blocks 54 and 56. The wedge blocks 72 and 74 are actuated by a shouldered adjusting screw 76 which is comparable to the shouldered adjusting screw 60 which was previously described. A cup 78 is screwed to sleeve 66 in a manner which will encompass the ball 52a. The combination may be rotated about the ball, and may be tilted to any desired compound angle. Tightening the screw 76 will apply pressure to releasably retain the position to which the cast mounting plate 64 is adjusted.

The combination of elements described to this point will produce the following controllable movements as schematically indicated in FIG. 1: (1) the body element 38 has lateral, longitudinal and angular movement in relationship with leaf element 16, (2) the rod 52 has vertical movement in body element 38, and, (3) the cast mounting plate 64 has rotational and tilting or canting movement to any compound angle on the ball 52a.

One species of the lower dental cast mounting jig is depicted in FIG. 2, and in cross-section in FIG. 3. The lower dental cast is removably mounted on a cast mounting plate 80 which is comparable to cast mounting plate 64 on the upper cast mounting jig. Attached to the lower face of the mounting plate 80 is a conventional dove-tail slide 82 which may be attached by means of screws 84 as shown in FIG. 3. The slide 82 is movable in a suitable dove-tail groove machines in platform 86 as depicted in FIG. 2. The selected position of the slide in the platform is releasably maintained by means of a conventional screw 88 which is threadably supported in the platform 86 and applying pressure against the dove-tail slide 82.

The platform 86 has a downwardly extending stem 86a which passes through an aperture in the base element 12 as best seen in FIG. 3, and a comparable coaxial aperture in block 90 which is held in position below base element 12 by a plurality of screws 92 as shown in FIG. 2.

As most easily seen in FIG. 3, the block 90 has a circular aperture 90a which is comparable to circular aperture 58 and contains wedge blocks 94 and 96 which are comparable to wedge blocks 54 and 56 which were previously described in detail. A shouldered adjusting screw 98 which is comparable to shouldered adjusting screw 60 actuates the wedge blocks 94 and 96.

If the lower mounting jig is to have vertical movement, without capability for rotational movement, the stem 86a is provided with flats as depicted on rod 52 in FIG. 7, and the wedge blocks 94 and 96 would be provided with comparable flats as previously described for wedge blocks 54 and 56. If however, rotational movement of the lower mounting jig is desired, the stem 86a would be round (without flats) and the flat faces on the wedge blocks 94 and 96 would be replaced by arcuate faces for gripping the stem 86a when the adjusting screw is tightened.

The combination of elements described as constituting the lower cast mounting jig will produce the following controllable movements as schematically indicated in FIG. 1; (1) the jig may be moved vertically, (2) the jig may be moved laterally, and (3) the jig may be moved rotationally if the stem 86a is round and the wedge blocks 94 and 96 are formed with arcuate faces for gripping the stem.

If lateral movement of the lower cast mounting jig is not required, the dove-tail slide 82 and the adjusting screw 84 may be omitted, and cast mounting plate 80 would be attached directly to the platform 86. The lateral movement is worth the additional cost because it is useful in centering the lower dental cast in the articulator.

The technique for producing poured dental casts used in the fabrication of dentures is well known and has been used for many years. As a very brief description, such casts are poured in impressions taken in the oral cavity of a patient, and after the casts have hardened, the casts are trimmed to size on a sanding disc.

When using one of the species of the articulator constituting the present invention, the next step is to prepare the dental casts for mounting in the articulator. This is most easily accomplished by using a drill jig specifically designed for such purpose.

Specific reference is made to FIGS. 8–11 which depict a drill jig designed for preparing a hardened and trimmed dental cast for mounting in an articulator, and also showing the preferred method for using the drill jig. The drill jig is preferably used with a horizontal dental lathe which is a necessary tool in every dental laboratory. The preferred cutting tool is a standard burr which is also used in every laboratory; however, other cutting tools may be used.

Figure 8:
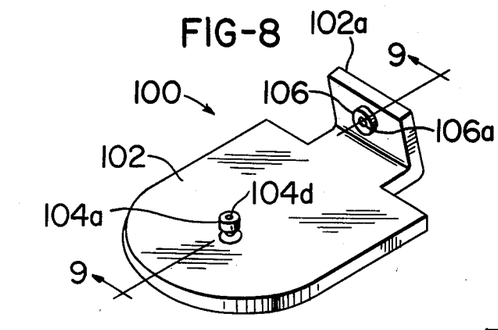
FIG. 8 is a perspective of the drill jig used to drill apertures or detents in the dental casts to be mounted.

The drill jig 100 has a body 102 which may be a replica of the cast mounting plates 64 and 80, and which may be formed in the same dies used in forming the mounting plates. The purpose of the drill jig is to permit the cutting of an aperture in the base of each dental cast, and to permit the cutting of an aperture into the perimeter of each cast which is in radial alignment with the aperture in the base of the cast. As will be explained below, the apertures in the casts form the alignment and retention points when mounting the casts in the articulator.

Figure 9:
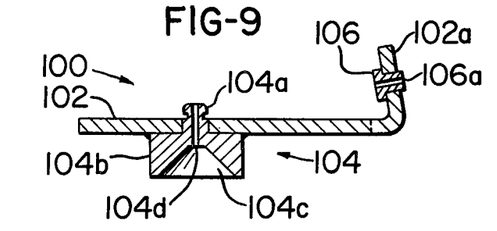
FIG. 9 is a vertical cross-section taken on line 9—9 of FIG. 8.
Figure 10:
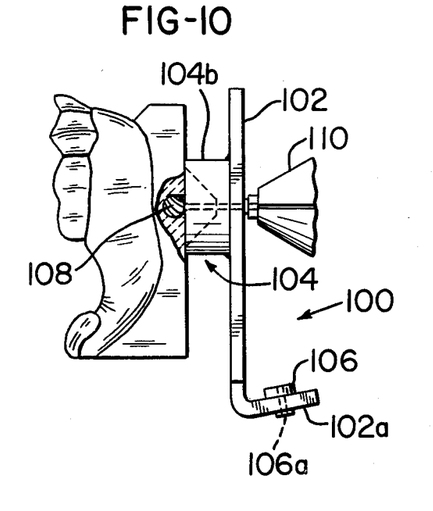
FIG. 10 illustrates the drilling of an aperture in the base of a dental cast; and, FIG. 11 illustrates the drilling of an aperture or detent in the perimeter of a dental cast.

A combination cupped drill guide and locating pin 104 is permanently attached to body 102 as depicted in FIG. 9. The locating pin portion 104a protrudes from the face of the jig which corresponds to the faces of the mounting plates 64 and 80 against which the casts are to be mounted in the articulator. The cup end 104b protrudes from the opposing face of the body 102, and has a cavity 104c which is somewhat deeper than the burr to be used in order that the burr may be retracted from the rim of the cup into the cavity. The cavity also has the function of collecting debris which forms when the burr is cutting a cavity in the base of a cast as depicted in FIG. 10. An aperture 104d is longitudinally coaxial with the locating pin portion 104a, and is of such diameter as will form a running fit on the stem of the burr.

The upturned portion 102a, as depicted, contains a steel guide 106 having a longitudinal aperture 106a therethrough which is in radial alignment with, and of the same diameter as the aperture 104d through the drill guide and locating pin 104. The reason why the upturned portion 102a is not perpendicular with the larger portion of the body 102 will be explained when describing the manner of mounting the casts in the articulator.

In using the drill jig for cutting an aperture in the base of a dental cast, the jig is slipped onto the stem of a burr 108 as depicted in FIG. 10, and the end of the stem is gripped by the collet 110 of a standard horizontal dental lathe. With the burr retracted into the cavity 104c, the cup end 104b is visually aligned in the central region on the base of the dental cast to place it in the position at which it is desired to drill a cavity with the burr. The drill jig and the dental cast are held together in this position with the hands, and, while the dental lathe is rotating the burr, the cast is moved in the direction of the burr.

As illustrated in FIG. 10, the cast and the drill jig are moved in the direction of the burr until the top face of the locating pin portion 104a is against the collet 110. This is a convenient method for controlling the depth of the aperture being cut into the base of the cast. Experience will soon show an operator how much clearance is initially required between the drill jig and the collet on the dental lathe to produce a cavity of desired depth in the base of the cast.

Figure 11:
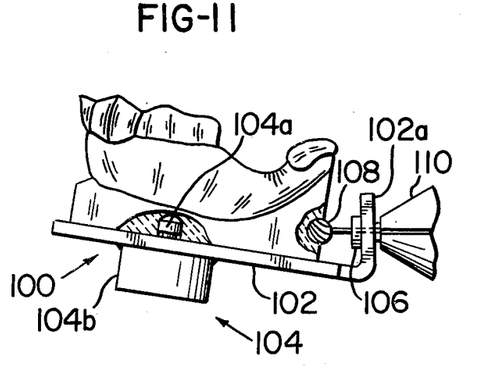

After the cavity has been drilled into the base of the cast as illustrated in FIG. 10, the cast is removed, and the jig and burr are removed from the dental lathe. The burr is then transferred to guide 106 as depicted in FIG. 11. The cast is then repositioned on the drill jig 100 as depicted in FIG. 11 with locating pin portion 104a entering the cavity previously drilled into the base of the cast. The drilling operation, which was described above, is then repeated while holding the cast in position on the drill jig. The cast has now been prepared for mounting in the articulator.

Specific reference is again made to FIG. 2 which illustrates the manner in which the prepared casts are mounted in the articulator. Both the upper and the lower cast mounting jigs in the articulator have a protruding mounting or locating pin 112 for entering the aperture drilled in the base of each cast by the burr. Each cast is held in fixed position by a holding screw 114 passing through a threaded aperture in the cast mounting plates 64 and 80. The end of each holding screw is contoured to fit the bottom of the cavity which it engages; in the drawings, the contour is spherical since the cavities were cut with a spherical burr.

Although not absolutely necessary if care is used in drilling the apertures in the perimeter of the dental casts, it has been found preferable to drill the apertures at about a 10 degree inclination as depicted. When tightening the holding screws, there is a vertical thrust component acting to hold the casts firmly against their mounting plates. It has also been found that if the national fine thread series is used on all holding screws, lock nuts are not required to prevent the screws holding the casts in place from tending to work loose. The casts may be repeatedly removed and remounted to their precise original position.

FIG. 4 depicts a simple non-adjustable lower cast mounting jig. A mounting pin 112 is pressed into the base element 12. A bracket 116 is substituted for cast mounting plate 80, and is held in place with screws 118. The upper cast mounting jig has all the necessary movements required to adjust an upper mounted dental cast in centric occlusal relationship with a fixed position mounted lower dental cast. Although this arrangement is not as flexible as one in which the lower cast may also be adjusted, it will suffice for many dentures to be fabricated.

Within the scope of the present invention and the appended claims, articulators may be built which have various combinations of movements in the upper and lower mounting jigs. For example, and in addition to the combinations depicted and described for illustrative purposes, the lower mounting jig may incorporate a cast mounting plate capable of having rotational and canting movement about a ball which is comparable with ball 52a depicted in FIG. 3. This combination is used when a dentist wishes to use a conventional face bow in connection with the mounting of dental casts made from impressions taken in the oral cavity of an edentulous patient. The face bow is primarily used to establish the horizontal plane in the articulator which is comparable to the horizontal plane in the patient's oral cavity to which the dentures are to be oriented when they are worn by the patient.

The basic requirement is that, in combination, an articulator have sufficient movements divided between the upper and the lower cast mounting jigs to permit adjusting the casts after they are mounted in the articulator, regardless of whether the upper cast is adjusted to the lower cast, or, the lower cast is adjusted to the upper cast.

It is to be understood that the embodiments of the present invention as shown and described are to be regarded as merely illustrative, and that the invention is susceptible to variations, modifications and changes, without regard to specific construction methods, within the scope of the appended claims.

We claim:

1. A dental articulator for releasably mounting and adjusting matched upper and lower dental casts used for the fabrication of dentures and having a pre-formed aperture in the base of said casts, and a pre-formed aperture in the perimeter of said casts, said articulator comprising:
    (a) an articulator body having a base element, at least one vertical element, and a normally horizontal leaf element pivotally supported at the upper end of said vertical element;
    (b) a lower dental cast mounting jig supported by the base element of said articulator body, said lower mounting jig having an upward protruding locating pin for engaging the pre-formed aperture in the base of said lower dental cast, and holding means having a contoured member at one end thereof for engaging the pre-formed aperture in the perimeter of said lower dental cast and releasably holding said lower cast in mounted position on said lower mounting jig; and,
    (c) an upper dental cast mounting jig adjustably supported by the leaf element of said articulator body, said upper mounting jig having a downward protruding locating pin for engaging the pre-formed aperture in the base of said upper dental cast, holding means having a contoured member at one end thereof for engaging the pre-formed aperture in the perimeter of said upper dental cast and releasably holding said upper dental cast in mounted position on said upper cast mounting jig, said upper cast mounting jig in combination with said lower cast mounting jig having adjusting means for adjusting said mounted dental casts in anatomical centric relationship with each other.

2. A dental articulator in accordance with claim 1 in which said upper dental cast mounting jig is longitudinally and laterally adjustable on the leaf element of said articulator body.

3. A dental articulator in accordance with claim 1 in which said upper dental cast mounting jig is longitudinally, laterally and angularly adjustable on the leaf element of said articulator body.

4. A dental articulator in accordance with claim 1 in which said lower dental cast mounting jig is adjustable on the base element of said articulator body.

5. A dental articulator in accordance with claim 1 in which said lower dental cast mounting jig is vertically and rotatably adjustable on the base element of said articulator body.

6. A dental articulator in accordance with claim 1 in which said lower dental cast mounting jig is vertically, laterally and rotatably adjustable on the base element of said articulator body.

7. A dental articulator in accordance with claim 1 in which said holding means for engaging the apertures in the perimeter of said upper and said lower dental casts are screw means.

8. A dental articulator for releasably mounting and adjusting matched upper and lower dental casts used for the fabrication of dentures and having a pre-formed aperture in the base of said casts, and a pre-formed aperture in the perimeter of said casts, said articulator comprising:
    (a) an articulator body having a base element, at least one vertical element, and a normally horizontal leaf element pivotally supported at the upper end of said vertical element;
    (b) a lower dental cast mounting jig supported by the base element of said articulator body, said lower mounting jig having an upward protruding locating pin for engaging the pre-formed aperture in the base of said lower dental cast, and holding means having a contoured member at one end thereof for engaging the pre-formed aperture in the perimeter of said lower dental cast and releasably holding said lower cast in mounted position on said lower mounting jig; and,
    (c) an upper dental cast mounting jig adjustably supported by the leaf element of said articulator body, said upper mounting jig having a downward protruding locating pin for engaging the pre-formed aperture in the base of said upper dental cast, holding means having a contoured member at one end thereof for engaging the pre-formed aperture in the perimeter of said upper dental cast and releasably holding said upper dental cast in mounted position on said upper cast mounting jig, and further having adjusting means for adjusting said mounted upper dental cast in anatomical centric relationship with said mounted lower dental cast.

9. A dental articulator in accordance with claim 8 in which said upper dental cast mounting jig is longitudinally and laterally adjustable on the leaf element of said articulator body.

10. A dental articulator in accordance with claim 8 in which said upper dental cast mounting jig is longitudinally, laterally and angularly adjustable on the leaf element of said articulator body.

11. A dental articulator in accordance with claim 8 in which said lower dental cast mounting jig is adjustable on the base element of said articulator body.

12. A dental articulator in accordance with claim 8 in which said lower dental cast mounting jig is vertically and rotatably adjustable on the base element of said articulator body.

13. A dental articulator in accordance with claim 8 in which said lower dental cast mounting jig is vertically, laterally and rotatably adjustable on the base element of said articulator body.

14. A dental articulator in accordance with claim 8 in which said holding means for engaging the apertures in the perimeter of said upper and lower dental casts are screw means.

15. A dental articulator for releasably mounting and adjusting matched upper and lower dental casts used for the fabrication of dentures and having a pre-formed aperture in the base of said casts, and a pre-formed aperture in the perimeter of said casts, said articulator comprising:
   (a) an articulator body having a base element, at least one vertical element, and a normally horizontal leaf element pivotally supported at the upper end of said vertical element;
   (b) a lower dental cast mounting jig supported by the base element of said articulator body, said lower mounting jig having an upward protruding locating pin for engaging the pre-formed aperture in the base of said lower dental cast, and holding means having a contoured member at one end thereof for engaging the pre-formed aperture in the perimeter of said lower dental cast and releasably holding said lower cast in mounted position on said lower mounting jig; and,
   (c) an upper dental cast mounting jig having a normally horizontal longitudinally elongated body element the rear end of which is adjustably supported by the leaf element of said articulator body and with the front end superimposed above said lower cast mounting jig, a vertical adjustment rod adjustably supported by the forward end of said body element and having a ball at the lower end of said vertical adjustment rod, a cast mounting plate adjustably supported on the ball at the lower end of said vertical adjustment rod, said cast mounting plate having a lower face thereon with a downward protruding locating pin for engaging the pre-formed aperture in the base of said upper dental cast, said cast mounting plate being adapted for rotational and canting movement on the ball of said vertical adjustment rod, and holding means having a contoured member at one end thereof for engaging the pre-formed aperture in the perimeter of said upper dental cast and releasably holding said upper dental cast in mounted position against the lower face of said cast mounting plate, said upper cast mounting jig being adapted for adjusting said mounted upper dental cast in anatomical centric relationship with said mounted lower dental cast.

16. A dental articulator in accordance with claim 15 in which the body element of said upper cast mounting jig is of general bowed shape with the front portion thereof substantially parallel with but at a higher elevation than the rear portion of said body element.

17. A dental articulator in accordance with claim 15 in which the body element of said upper cast mounting jig is laterally, longitudinally and angularly adjustable on the leaf element of said articulator body and is of general bowed shape with the front portion thereof substantially parallel with but at a higher elevation than the rear portion of said body element.

18. A dental articulator in accordance with claim 15 in which said holding means for engaging the apertures in the perimeter of said upper and said lower dental casts are screw means.

19. A dental articulator in accordance with claim 15 in which said lower dental cast mounting jig is adjustable on the base element of said articulator body.

20. A dental articulator in accordance with claim 15 in which said lower dental cast mounting jig is vertically and rotatably adjustable on the base element of said articulator body.

21. A dental articulator in accordance with claim 15 in which said lower dental cast mounting jig is vertically, laterally and rotatably adjustable on the base element of said articulator body.

22. A drill jig for use with a cutting tool in forming a first aperture in the base of a hardened dental cast, and a second aperture in the perimeter of said dental cast; said drill jig comprising:
   (a) a body having a major element with a flat upper face and a minor element upturned from the upper face of said body;
   (b) a combination drill guide and locating pin joined to said body with the locating pin protruding from and perpendicular with the upper face of said body and having a coaxial cup end extending downward from the lower face of said body, the drill guide being a longitudinal aperture coaxial with said locating pin and said cup end; and,
   (c) a drill guide having an aperture therethrough and joined to the minor element of said body with the aperture through said drill guide being in radial alignment with the locating pin on said combination drill guide and locating pin.

23. A drill jig in accordance with claim 22 in which said drill guide in the minor element of said body is inclined downward from the horizontal plane in the direction of the locating pin in said combination drill guide and locating pin.

* * * * *